(12) United States Patent
Joss et al.

(10) Patent No.: US 6,346,819 B1
(45) Date of Patent: *Feb. 12, 2002

(54) METHOD AND DEVICE FOR DETERMINING PROPORTIONS OF SOLID MATTER IN A TEST MATERIAL

(75) Inventors: Rolf Joss, Horgen; Paul Geiter, Freienbach, both of (CH)

(73) Assignee: Zellweger Luwa AG, Uster (CH)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/212,257

(22) Filed: Dec. 16, 1998

(30) Foreign Application Priority Data

Dec. 18, 1997 (CH) .............................. 2918/97

(51) Int. Cl.[7] .............................. G01R 27/26
(52) U.S. Cl. .............................. 324/665
(58) Field of Search .............................. 324/665, 688, 324/667, 669, 439, 639

(56) References Cited

U.S. PATENT DOCUMENTS

| | | | | | |
|---|---|---|---|---|---|
| 4,240,027 A | | 12/1980 | Larsen et al. | | |
| 4,429,272 A | * | 1/1984 | Bungay | | 324/665 |
| 4,845,421 A | * | 7/1989 | Howarth et al. | | 324/688 |
| 4,928,065 A | * | 5/1990 | Lane et al. | | 324/439 |
| 5,450,015 A | * | 9/1995 | Mastico et al. | | 324/665 |
| 5,455,516 A | * | 10/1995 | Jean et al. | | 324/639 |
| 5,594,163 A | | 1/1997 | Suzuki | | |

FOREIGN PATENT DOCUMENTS

EP 0390093 A2 10/1990

* cited by examiner

Primary Examiner—Safet Metjahic
Assistant Examiner—J Kerveros
(74) Attorney, Agent, or Firm—Burns, Doane, Swecker & Mathis LLP

(57) ABSTRACT

The invention relates to a method and a device for determining proportions of solid matter in a test material. In order to reliably and easily determine proportions of solid matter in a test material, even in the case of transparent matter or matter of a similar color to the test material, the test material is exposed to an electric field and dielectric properties of the field are determined with the test material present. Two electrical quantities are determined from the dielectric properties and combined, resulting in a characteristic value which is independent of the mass of the test material. The characteristic value is compared with a previously determined characteristic value for the matter in question and the proportion of solid matter is determined therefrom.

24 Claims, 3 Drawing Sheets

METHOD AND DEVICE FOR DETERMINING PROPORTIONS OF SOLID MATTER IN A TEST MATERIAL

BACKGROUND OF THE INVENTION

The present invention relates to a method and a device for determining proportions of solid matter in a test material.

One example of a situation in which it is desirable to determine proportions of solid matter in a test material is in the detection of foreign matter and foreign fibers in a textile formation. In this case the detection is usually carried out by optical means. For example, foreign matter and foreign fibers are detected by their reflection properties, which in the majority of known cases differ from the reflection properties of a pure textile formation. The textile formation to be tested is therefore illuminated with light. The light absorbed by the test material and/or the reflected light is then detected. Instantaneous or local deviations of the received quantity of light give an indication of the proportion of desirable and undesirable matter.

A disadvantage of known methods and devices of this kind lies in the failure to detect colorless, transparent or translucent matter such as, for example, polypropylene sheets, or matter of a color which is similar to that of the textile formation, such as cables or cords, which are used when packing raw textile materials such as cotton, etc. This results in parts of such polypropylene sheets, cables and cords being subsequently processed with the raw material, with the result that these are later enclosed in a yarn, for example.

It is possible to detect solid matter such as polypropylene parts when spun in a yarn. In this respect it is assumed that this matter or these polypropylene parts change the structure of the yarn and, for example, the hairiness in a section of the yarn in particular. This is detected when measuring the diameter, for example by a change in the mass of the yarn or in the hairiness due to polypropylene parts projecting from the yarn instead of hairs. Attempts have therefore been made in this case to detect foreign parts by measuring the diameter, the mass or the hairiness.

One disadvantage of this detection of proportions of solid matter or of foreign matter by measuring the diameter or the hairiness lies in the fact that much of the foreign matter is not detected. This is primarily due to the fact that it is not located at the surface of the test material. As a result, unfavorable proportions of solid matter and other foreign matter give rise to an end product which is weakened or contains defects. A product of this kind may also be the cause of difficulties during subsequent processing, so that a defect-free end product cannot be produced.

SUMMARY OF THE INVENTION

The present invention solves the object of providing a method and a device by means of which proportions of solid matter in a test material can be easily and reliably determined, even in the case of transparent matter or matter of a similar color as the test material.

This result is achieved by exposing the test material to an electric field and determining dielectric properties of the field with the test material. In order to determine the dielectric properties of the field, electrical measurable quantities are measured, from which at least two electrical quantities are determined and combined, resulting in a characteristic value which is independent of the mass of the test material. The characteristic value is compared with comparative values, and information on the proportion of solid matter or the change thereof in the test material is obtained from the comparison. The dielectric properties can be detected on the basis of a plurality of electrical quantities.

A first possibility lies, for example, in determining, as an electrical quantity, the change in capacitance caused by the test material or the relative permittivity $\in_r$ in an electric alternating field of at least two frequencies from measurable quantities such as voltage, current, phase shift between voltage and current and any reference resistances, and forming therefrom a quotient as a characteristic value.

A second possibility lies, for example, in determining, as a characteristic value, electrical quantities such as the power factor $\cos \phi$ of the change in capacitance caused by the test material from measurable quantities such as voltage, current, phase shift between voltage and current and any reference resistances.

The characteristic value determined from the electrical quantities by, for example, forming a quotient, remains constant as long as the proportion of solid matter in the test material remains constant. Should the proportion change, this fact is indicated by a corresponding change in the characteristic value. The absolute proportion of solid matter in the test material may also be determined by forming a relation from the constant characteristic value and from the changed characteristic value.

A device for performing this method consists of at least one precision capacitor, which is disposed in the region of the test material to create an electric field, a frequency generator connected to the capacitor to generate at least one frequency in the electric field, measuring elements connected to the frequency generator for electrical measurable quantities, and an evaluation circuit for forming the electrical quantities and the characteristic value and for comparing the characteristic value with predetermined values.

In order to be able to cancel out the basic capacitance of the capacitor without the test material, a reference capacitor, connected to the same or to an inverted signal source, may be provided. The frequency generators preferably form a bridge circuit with the precision capacitor and the reference capacitor.

The dielectric properties of a field are represented by at least one quantity from a group of electrical quantities comprising capacitance, relative permittivity, loss angle and power factor.

The advantages achieved by the invention lie in particular in the fact that it enables the most varied foreign matter, compositions or proportions of solid matter in a test material to be detected, irrespective of whether certain matter is visible, invisible or of a similar color to the test material or whether it occurs inside or at the surface. The means provided for carrying out the method are of a simple structure and allow it to be combined problem-free with other measuring devices which measure other parameters in pursuit of other objects.

BRIEF DESCRIPTION OF THE DRAWINGS

The invention is illustrated in detail in the following on the basis of an example and with reference to the accompanying figures, in which.

DETAILED DESCRIPTION

Figure 1:
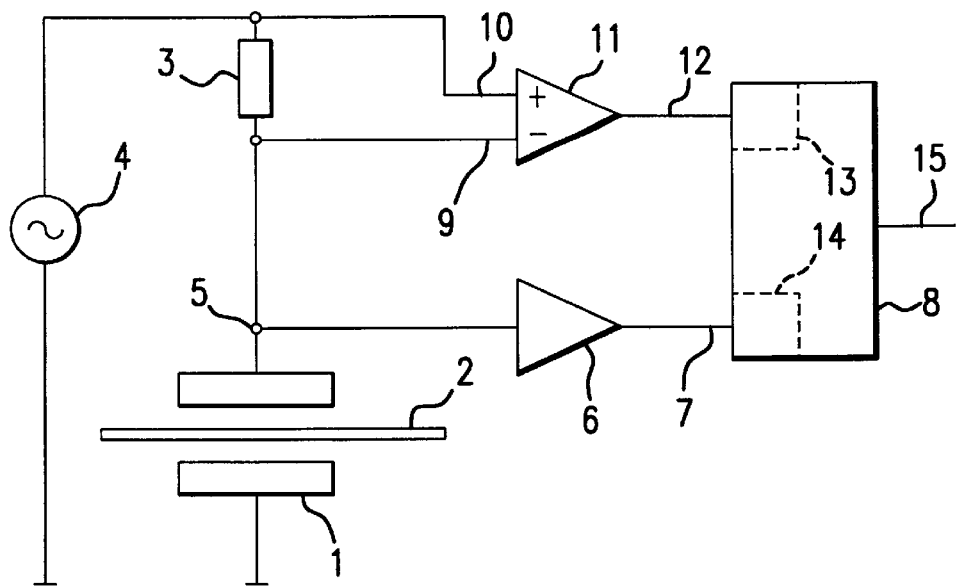
FIG. 1 is a diagrammatic and simplified representation of a first device in accordance with the present invention.

FIG. 1 shows a first embodiment of a device according to the invention with a precision capacitor 1 for an elongate test material 2 that is moved longitudinally such as, for example, a yarn, roving, tape, filament, etc. The precision capacitor 1 is connected on one side, via a resistor 3, to a frequency generator 4 and on the other side to a ground reference potential. One output 5 of the precision capacitor 1 is connected via an amplifier 6 to one input 7 of an evaluation circuit 8. The same output 5 is also connected to one input 9 and, via the resistor 3, to the other input 10 of an operational amplifier 11, which is connected in parallel with the resistor 3. The output of the operational amplifier 11 forms a further input 12 for the evaluation circuit 8. The inputs 7 and 12 are respectively connected in the evaluation circuit 8 to measuring elements 13, 14, which are known per se, for electrical quantities. The evaluation circuit 8 has an output 15.

Figure 2:
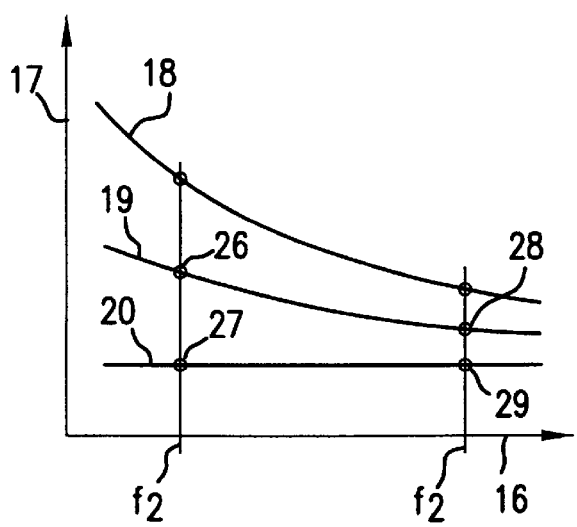
FIGS. 2 and 3 are graphical representations of physical relations.

FIG. 2 is a graphical representation of characteristic signals along two axes 16 and 17. Values for frequencies of an electric field are plotted along the axis 16 and values for the relative permittivity $\in_r$ of the same field along the axis 17. Curves 18, 19 and 20 represent the relative permittivity $\in_r$ as a function of the frequency for fields with a test material of cotton with 68% moisture, of cotton with 47% moisture and of polypropylene. It can be seen here that the relative permittivity for polypropylene according to curve 20 is largely independent of frequency, while the relative permittivity for cotton is highly frequency-dependent, as shown by the curves 18 and 19. The frequency dependency increases with the moisture content. As the change in capacitance of the precision capacitor changes proportionally with the relative permittivity, the same relative dependency on frequency applies to the change in capacitance. However the change in capacitance is at the same time also influenced by the mass of the test material.

Figure 3:
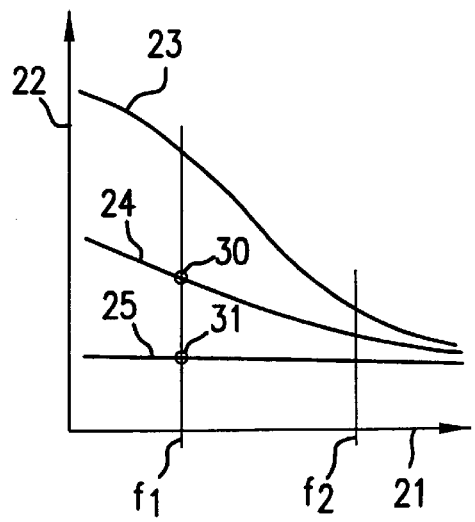

FIG. 3 is a graphical representation of other characteristic signals with two axes 21 and 22. Values for frequencies of an electric field are plotted along the axis 21 and values for the power factor cos φ of the test material, for different materials, along the axis 22. Curves 23, 24 and 25 represent the power factor cos φ as function of the frequency for cotton with 68% moisture, for cotton with 47% moisture and for polypropylene as the test material. Whereas the power factor of polypropylene is largely independent of frequency, the power factor of cotton is highly frequency dependent. Here too the dependency increases with the moisture content of the cotton. However the power factor of the change in capacitance of the precision capacitor is independent of the mass of the test material.

Figure 4:
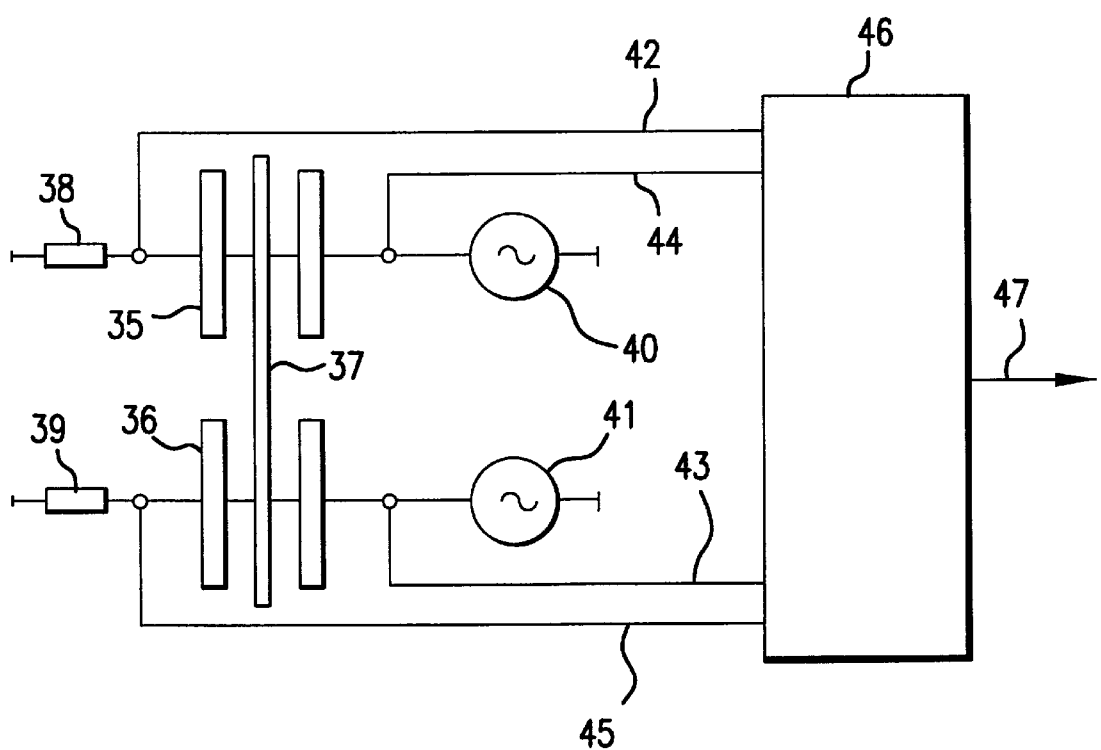
FIGS. 4 to 6 are further embodiments of the device according to the invention.

FIG. 4 shows a second embodiment of a device according to the invention with two precision capacitors 35 and 36 for an elongate test material 37 that is moved longitudinally such as, for example, a yarn, roving, tape, filament, etc. The precision capacitors 35, 36 are connected on one side, via resistors 38, 39, to a ground potential and on the other side to a respective frequency generator 40, 41. The precision capacitors 35, 36 are connected via lines 42, 44 and 43, 45 to an evaluation unit 46 which, for example, is formed as a processor and has an output 47.

Figure 5:
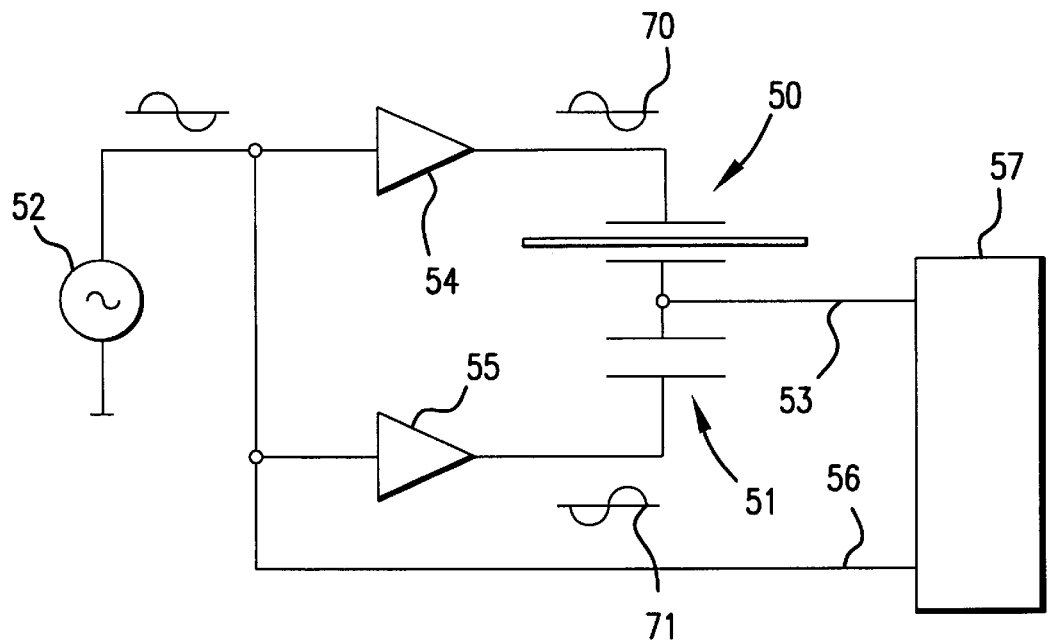

FIG. 5 is a simplified representation of a third embodiment with a precision capacitor 50, a reference capacitor 51 and a frequency generator 52. A tap 53 lies between the capacitors 50 and 51, and an inverting or non-inverting amplifier 54, 55, is respectively associated with each. Also provided is an evaluation circuit 57, which is connected via the tap 53 and a line 56.

Figure 6:
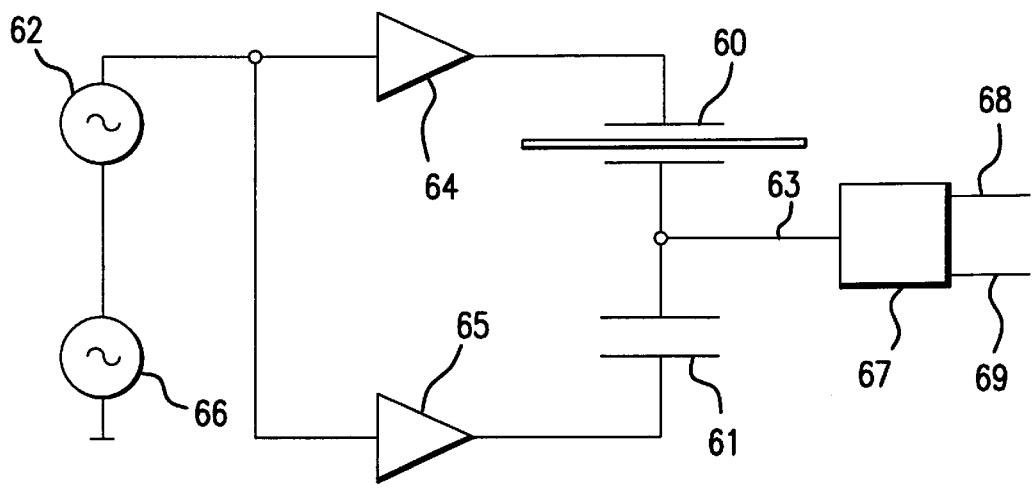

FIG. 6 is a simplified representation of a fourth embodiment with a precision capacitor 60, a reference capacitor 61 and a frequency generator 62. A tap 63 lies between the capacitors 60 and 61, and each is associated with an inverting or non-inverting amplifier 64, 65, respectively. Another frequency generator 66 is also connected in series with the frequency generator 62. The tap 63 leads into an element 67 for frequency separation with two outputs 68, 69.

The invention operates as follows:

In order to determine proportions of solid matter such as, for example, the proportion of polypropylene in a cotton yarn or cotton tape, the test material, e.g. the cotton yarn or cotton tape, is placed in an electric alternating field which is generated with alternating current at a certain frequency f1. This produces an electric alternating field whose dielectric properties are determined not just by measurable values such as current, voltage and phase angle, but also by the preset frequency. The dielectric properties may be expressed in particular by the relative permittivity $\in_r$ and/or the power factor cos φ. It is also possible to repeat this operation in further electric alternating fields with further frequencies f2, f3, etc. and then also obtain second, third, etc. differing values for the relative permittivity $\in_r$ and the power factor cos φ.

If the values which express the dielectric properties for the matter present in the test material are known separately, as represented, for example, in FIGS. 2 and 3, the proportion of the matter in the test material can be determined from these. There are various possibilities for this.

A first possibility lies in determining the change in capacitance AC of the precision capacitor, as a consequence of a test material introduced therein, for at least two frequencies f1, f2, ... of the measuring field in the precision capacitor from the dielectric properties and the quantity of matter. This is effected on the one hand for pure test material such as polypropylene or cotton by calculation with values from FIG. 2 and on the other hand by measuring corresponding values of the dielectric properties at the precision capacitor with actual test material. Assuming that the test material consists of two types of matter, the change in capacitance of the precision capacitor with a test material consisting of just one of these types of matter in each case can be calculated using values from FIG. 2. From this it is possible to determine the change in capacitance of the precision capacitor with pure and with actual test material at two or more frequencies. A quotient can be determined as the characteristic number from the determined changes in capacitance at different frequencies for the test material, this quotient ideally being 1 for polypropylene and greater than or less than 1 for cotton, for example. This characteristic number is independent of the mass of the test material and can be continuously monitored for actual test material by comparison with a reference value. The occurrence of a deviation means that the proportion of foreign matter in the test material has changed. Alternatively, the proportion of pure matter in the actual test material can be quantified from a formula, with the characteristic number for a pure test material and the characteristic number for the actual test material.

A second possibility lies in determining in a known manner, from the electrical measurable quantities which characterize an electric field, the power factor cos φ of the change in capacitance caused by the test material introduced into the field. This power factor is independent of the mass of the test material, which is why it is sufficient to determine the power factor for pure test material and the power factor for actual test material. A characteristic number which is proportional to the proportion of one of the types of matter in the test material can be determined from the two power factors according to a formula and can also be monitored.

In the device according to FIG. 1, the test material 2 in the precision capacitor 1 is exposed to an electric field with a frequency f1. The precision capacitor 1 is fed with appropriate alternating currents from the frequency generator 4 via the resistor 3, resulting in an alternating field with a frequency f1 in the gap in the precision capacitor 1. The voltage at the output 5 of the precision capacitor 1 is amplified in the amplifier 6 and applied to the input 7, so that this voltage is quantified in the measuring element 14 and then fed to the evaluation circuit 8. The voltage across the resistor 3 is amplified in the operational amplifier 11 and fed via the input 12 to the measuring element 13, where it is likewise quantified. Since the value of the resistor 3 is known, the evaluation circuit 8 can also calculate the current in the resistor 3 from this. The change in capacitance of the precision capacitor 1 caused by the test material can be determined according to laws which are known per se from this and from the fixed quantities known for the precision capacitor 1. The power factor cos φ is also determined by measuring the phase difference between the current and the voltage. The values for the power factor cos φ of the change in capacitance are independent of the mass of the test material 2 in the precision capacitor 1. This change in capacitance is determined in the evaluation circuit 8 using values from the measuring elements 13, 14 and other fixed inputs. The evaluation circuit 8 may be formed as an electric circuit or as a computer which digitally processes measured values and inputs. The evaluation circuit delivers via the output 15 a signal which indicates the presence of other solid matter in the test material or a changed proportion of one of the types of matter. A signal of this kind may be continuously delivered by the evaluation unit 8, processed to form mean values therein and compared with mean values of this kind or other reference values. Distinct deviations then point to changes in the composition of the test material 2.

In order to quantify the proportion of a solid matter in the test material 2, it is assumed that the matter forming the test material 2 is known. For example, the test material 2 consists of cotton with 47% moisture and possibly polypropylene. Power factors for this matter at arbitrary frequencies f1, f2 can be read from FIG. 3. Assuming that the proportions of both types of matter together amount to 100% of the mass of the test material 2, the proportion of the first matter can be determined according to the following formulae (1) and (2).

In the device according to FIG. 4 the test material is moved through two precision capacitors 35, 36 in succession, these producing fields of different frequencies f1, f2, as produced by a.c. voltages, which are supplied by the frequency generators 40, 41. The evaluation unit 46 therefore receives values for currents and voltages at two different frequencies in parallel via the lines 42 to 45. Changes in capacitance can be calculated from these values and, in turn, a characteristic number from these changes. All the values which are represented in FIG. 2 are stored as tables in the evaluation unit 46 for this purpose. The proportion of a first matter K1 in the test material is therefore obtained from $$K1=(A-F2)/(F1-F2). \quad \text{formula (1)}$$

The proportion of the second matter is obtained from $$K2=(A-F1)/(F2-F1). \quad \text{formula (2)}$$

Here the values F1 and F2 are the ratios of the relative permittivities of cotton and polypropylene at the first frequency f1 and at the second frequency f2. The factors F1 and F2 are therefore obtained by forming a quotient, for example, from the values 26/28 and 27/29 in FIG. 2. The parameter A corresponds to the quotient of the changes in capacitance in the precision capacitor for the actual test material or the characteristic number already known.

In the device according to FIG. 5 an a.c. voltage with a frequency is produced in the frequency generator 52, fed to the two amplifiers 54, 55 and from these applied to both capacitors 50, 51. A phase shift of 180° is produced in the amplifier 55, for example, by delaying the signal, so that the capacitors 50, 51 are each supplied with a signal 70, 71 which cancel each other out. A zero voltage is thus present at the tap 53 at least when there is no test material in the precision capacitor 50. All influences of the empty capacitors are in this way neutralized. The signal at the tap 53 changes as soon as a test material is introduced into the precision capacitor 50. The cosine of the phase angle of the signal is the inverse of the power factor cos φ of the test material in the precision capacitor 50 and independent of the quantity of test material. The mixture ratio of the two types of matter in the test material can be determined from the power factor by a simple rule of allegation with the values from FIG. 3 for the frequency of the applied a.c. voltage. This takes place in the evaluation circuit 57, which also receives via the line 56 information on the phase angle of the unamplified signal, which is not influenced by the capacitors 50 and 51, of the frequency generator 52.

The operations in the device according to FIG. 6 are identical to those in the device according to FIG. 5, although with the difference that a signal with two superimposed frequencies is applied to the capacitors 60, 61 by the two frequency generators 62, 66, which signal is resolved into its two frequencies in the element 67. The ratio of the two components in the test material can be determined as is known for the device according to FIG. 4. This construction, as well as that according to FIG. 5, has the advantage with respect to the construction according to FIG. 4 of the influence of the empty capacitor being compensated by the bridge circuit principle. The signal voltage is zero when the precision capacitor is empty and this voltage changes proportionally with the dielectric properties of the test material and the quantity thereof.

As this method enables the proportions of solid matter in a test material to be determined, a prerequisite is for proportions of non-solid matter, such as water, in one of the types of matter for measurement to be constant. For example, the moisture in the cotton must be known and constant before measuring takes place. However this is the case in the textile industry anyway, for most operations relating to the processing of raw materials take place in air-conditioned spaces.

The capacitive detection of foreign matter and the proportions thereof in a test material may be combined with known measurements of other parameters such as, e.g. uniformity, mass, etc., as a signal can be used both for measuring such parameters and for detecting the proportions of foreign matter. As mentioned above, the proportions of foreign matter can be determined by calculating the capacitance at a plurality of frequencies or by calculating the power factor at just one frequency. However it is also possible to do this by calculating the power factor for a plurality of frequencies. Suitable frequencies are, for example, 10 kHz to 100 kHz and 10 MHZ.

What is claimed is:

1. A method for determining the proportion of a foreign substance in a test yarn, comprising the steps of:
   generating an electric field by means of a capacitor;
   placing the test yarn within the electric field such that it influences dielectric properties of the capacitor;
   measuring changes in the capacitance of the capacitor resulting from the influence of the test yarn in which at least two electrical quantities are measured;
   combining said two measured quantities to produce a characteristic value which is independent of the mass of the test material; and
   calculating the proportion of foreign substance from the measured changes.

2. The method of claim 1 wherein said electric field is generated at two different frequencies, and said proportion is calculated from the ratio of the capacitance at said two frequencies.

3. The method of claim 1, wherein said electric field is measured at one frequency when determining a power factor.

4. The method of claim 1, wherein the test yarn is an elongate yarn and ran longitudinally and continuously through the electric field.

5. A method for determining the proportions of solid matter in a test material, comprising the steps of:
   placing the test material within an electric field;
   measuring dielectric properties of the electric field with the test material therein; and
   determining a proportion from the measured dielectric properties;
   wherein said measuring step comprises the measurement of at least two electrical quantities, and said determining step comprises combining said two measured quantities to produce a characteristic value which is independent of the mass of the test material.

6. The method of claim 5 wherein said electrical quantities are changes in capacitance for two different frequencies of the electric field.

7. The method of claim 5 wherein said characteristic value is compared with a previously determined characteristic value for a given solid matter, and said proportion is determined therefrom.

8. The method of claim 5 wherein said dielectric property comprises an electrical quantity which forms a characteristic value that is independent of the mass of the test material.

9. The method of claim 8 wherein said electrical quantity is power factor.

10. The method of claim 8 wherein said characteristic value is compared with a previously determined characteristic value for a given solid matter, and said proportion is determined therefrom.

11. The method of claim 5 wherein said electric field is generated at two different frequencies, and said proportion is determined from values for the dielectric properties which are measured at each of said two frequencies.

12. The method of claim 11 wherein two measured values are respectively obtained at said two frequencies, and said two measured values are combined to form a signal whose value is compared with a previously determined value to determine said proportion.

13. The method of claim 12 wherein said dielectric properties are determined from measured values related to currents, voltages and phase angles generated by said electric field.

14. The method of claim 5, wherein the test material is an elongate material and moved longitudinally through the electric field.

15. Apparatus for determining the proportion of solid matter in a test material, comprising:
    a frequency generator which generates an electric field having at least one characteristic frequency;
    a capacitor connected to said frequency generator and operatively disposed such that said solid matter influences the dielectric properties of said capacitor;
    a measuring device which measures an electrical quantity related to the dielectric properties of said capacitor; and
    an evaluation circuit which determines a characteristic value independent of the mass of the test material related to said proportion from said measured quantity.

16. The apparatus of claim 15 further including a reference capacitor which provides input to said evaluation circuit for determination of said proportion.

17. The apparatus of claim 16 wherein said two capacitors and said frequency generator are connected to form a bridge circuit.

18. The apparatus of claim 15 further including a second frequency generator which generates an electric field at a second frequency different from said characteristic frequency.

19. The apparatus of claim 18 wherein said frequency generators are connected in series to produce an electric field with two superimposed frequencies.

20. The apparatus of claim 15 wherein said test material is an elongate material that is moved longitudinally within said capacitor.

21. A method of determining the proportion of foreign substance in a test yarn, comprising the steps of:
    determining values of a plurality of characteristic dielectrical properties of an electrical field containing substances, wherein each characteristic dielectrical property is representative of a substance or material present in the electrical field;
    storing said values for said determined dielectrical properties;
    forming a set of first quotients of values obtained from said determined characteristic dieletrical properties;
    exposing the test yarn to an electric field and determining dielectric properties of the field with the test yarn by measuring at least two electrical quantities;
    determining a second quotient derived from changes in capacitance of the field, corresponding to said first quotient of values; and
    calculating the proportion of pure material in the test yarn using the second quotient obtained by measurements on the test yarn and the quotient of values obtained from the previously determined characteristic dielectrical properties.

22. The method of claim 21, wherein the characteristic dielectric properties comprise at least one of relative permittivity or real power and active power.

23. The method of claim 21, wherein the measuring of at least two electrical quantities includes relative permittivity measured at two different frequencies.

24. The method of claim 21, wherein the measuring of at least two electrical quantities includes values of real and active power to calculate the power factor.

* * * * *